United States Patent
Sivadas et al.

(10) Patent No.: US 12,185,972 B2
(45) Date of Patent: Jan. 7, 2025

(54) CUTTING APPARATUS

(71) Applicant: NuVasive, Inc., San Diego, CA (US)

(72) Inventors: Sujit Sivadas, San Diego, CA (US); Wei-Hsiang Chang, San Diego, CA (US); John C. Love, San Diego, CA (US)

(73) Assignee: Nuvasive, Inc., San Diego, CA (US)

( * ) Notice: Subject to any disclaimer, the term of this patent is extended or adjusted under 35 U.S.C. 154(b) by 564 days.

(21) Appl. No.: 17/519,707

(22) Filed: Nov. 5, 2021

(65) Prior Publication Data

US 2023/0143304 A1 May 11, 2023

(51) Int. Cl.
*A61B 17/3211* (2006.01)
*A61B 17/32* (2006.01)
*A61B 34/30* (2016.01)

(52) U.S. Cl.
CPC .......... *A61B 17/3211* (2013.01); *A61B 34/30* (2016.02); *A61B 2017/320052* (2013.01)

(58) Field of Classification Search
CPC ................ A61B 17/3211; A61B 34/30; A61B 2017/320052; A61B 17/32; A61B 17/32002
See application file for complete search history.

(56) References Cited

U.S. PATENT DOCUMENTS

| | | |
|---|---|---|
| 1,361,021 A | 12/1920 | Copeman |
| 1,368,842 A | 2/1921 | Roeling |
| 2,137,800 A | 11/1938 | Davey |
| 2,823,677 A | 2/1958 | Hein, Jr. |
| 3,247,592 A | 4/1966 | Arden |
| 3,262,205 A | 7/1966 | Arden |
| 3,900,950 A | 8/1975 | Collins |
| 4,064,871 A | 12/1977 | Reno |
| 4,157,086 A | 6/1979 | Maiorano |
| 4,438,770 A | 3/1984 | Unger |
| 4,643,189 A | 2/1987 | Mintz |
| 5,015,252 A | 5/1991 | Jones |
| 5,071,426 A | 12/1991 | Dolgin |
| 5,318,584 A | 6/1994 | Lange |
| 5,330,494 A | 7/1994 | Van Der Westhuizen |
| 5,431,672 A | 7/1995 | Cote |
| 5,437,101 A | 8/1995 | Collins |
| 5,476,474 A | 12/1995 | Davis |
| 5,529,581 A | 6/1996 | Cusack |
| 5,569,282 A | 10/1996 | Werner |
| 5,662,672 A | 9/1997 | Pambianchi |
| 5,797,940 A | 8/1998 | Mawhirt |
| 5,817,117 A | 10/1998 | Cartaxo |
| 5,938,676 A | 8/1999 | Cohn |
| 6,221,089 B1 | 4/2001 | Mawhirt |
| 6,358,265 B1 | 3/2002 | Thorne, Jr. |
| 7,101,382 B2 | 9/2006 | George |
| 7,223,275 B2 * | 5/2007 | Shiuey ............. A61F 9/0133 606/166 |
| 7,325,314 B1 | 2/2008 | Chen |

(Continued)

*Primary Examiner* — Tan-Uyen T Ho
*Assistant Examiner* — Khoa Tan Le

(57) ABSTRACT

An example cutting apparatus includes a scalpel and a housing defining a scalpel guide. A handle is coupled to a proximal end of the scalpel. A blade holder at a distal end of the scalpel. The scalpel has a length longer than a length of the housing. The scalpel guide constrains the movement path of the scalpel.

16 Claims, 8 Drawing Sheets

(56) References Cited

U.S. PATENT DOCUMENTS

| | | |
|---|---|---|
| 8,015,712 B2 | 9/2011 | Yi |
| 8,181,352 B1 | 5/2012 | Shackelford, Sr. |
| 8,291,601 B2 | 10/2012 | Kehr |
| 9,027,254 B1 | 5/2015 | Vodinh |
| 9,788,966 B2 | 10/2017 | Steinberg |
| 9,901,365 B1 | 2/2018 | Rosenhan |
| 10,092,314 B2 | 10/2018 | Castanon |
| 2004/0158269 A1 | 8/2004 | Holman |
| 2004/0181246 A1 | 9/2004 | Heppler |
| 2004/0250427 A1 | 12/2004 | Polei |
| 2005/0033341 A1* | 2/2005 | Vreeke .......... A61B 5/157 606/181 |
| 2006/0100650 A1 | 5/2006 | Kiehne |
| 2006/0241664 A1 | 10/2006 | Lam |
| 2009/0192538 A1 | 7/2009 | Sandel |
| 2010/0125293 A1 | 5/2010 | Auchter |
| 2012/0029542 A1 | 2/2012 | Huang |
| 2012/0210584 A1 | 8/2012 | Logan |
| 2012/0226299 A1 | 9/2012 | Heppler |
| 2013/0085516 A1 | 4/2013 | Kerr |
| 2013/0245656 A1 | 9/2013 | Austria |
| 2013/0303883 A1 | 11/2013 | Zehavi |
| 2014/0142600 A1 | 5/2014 | Kumar |
| 2014/0277107 A1 | 9/2014 | Ishida |
| 2015/0164539 A1 | 6/2015 | Kanigan |
| 2015/0190165 A1 | 7/2015 | Vodinh |
| 2015/0257777 A1 | 9/2015 | Woodward |
| 2016/0128712 A1 | 5/2016 | Ruggiero, Sr. |
| 2016/0128713 A1 | 5/2016 | Rauchwerger |
| 2016/0270816 A1 | 9/2016 | Mather |
| 2016/0303293 A1 | 10/2016 | Doyle |
| 2017/0112521 A1 | 4/2017 | Werner |
| 2017/0112522 A1 | 4/2017 | Hutchison |
| 2017/0135716 A1 | 5/2017 | Endo |
| 2018/0064497 A1* | 3/2018 | Hussain .......... A61B 34/30 |
| 2018/0242996 A1 | 8/2018 | Hutchison |
| 2019/0021795 A1 | 1/2019 | Crawford |
| 2019/0117320 A1 | 4/2019 | Shoham |
| 2020/0323559 A1 | 10/2020 | Skinner |
| 2021/0137535 A1* | 5/2021 | Sharifi-Mehr ......... A61B 34/30 |

\* cited by examiner

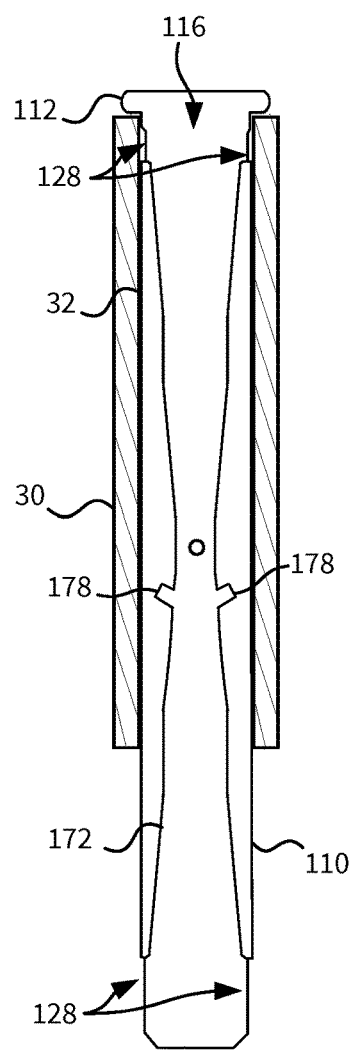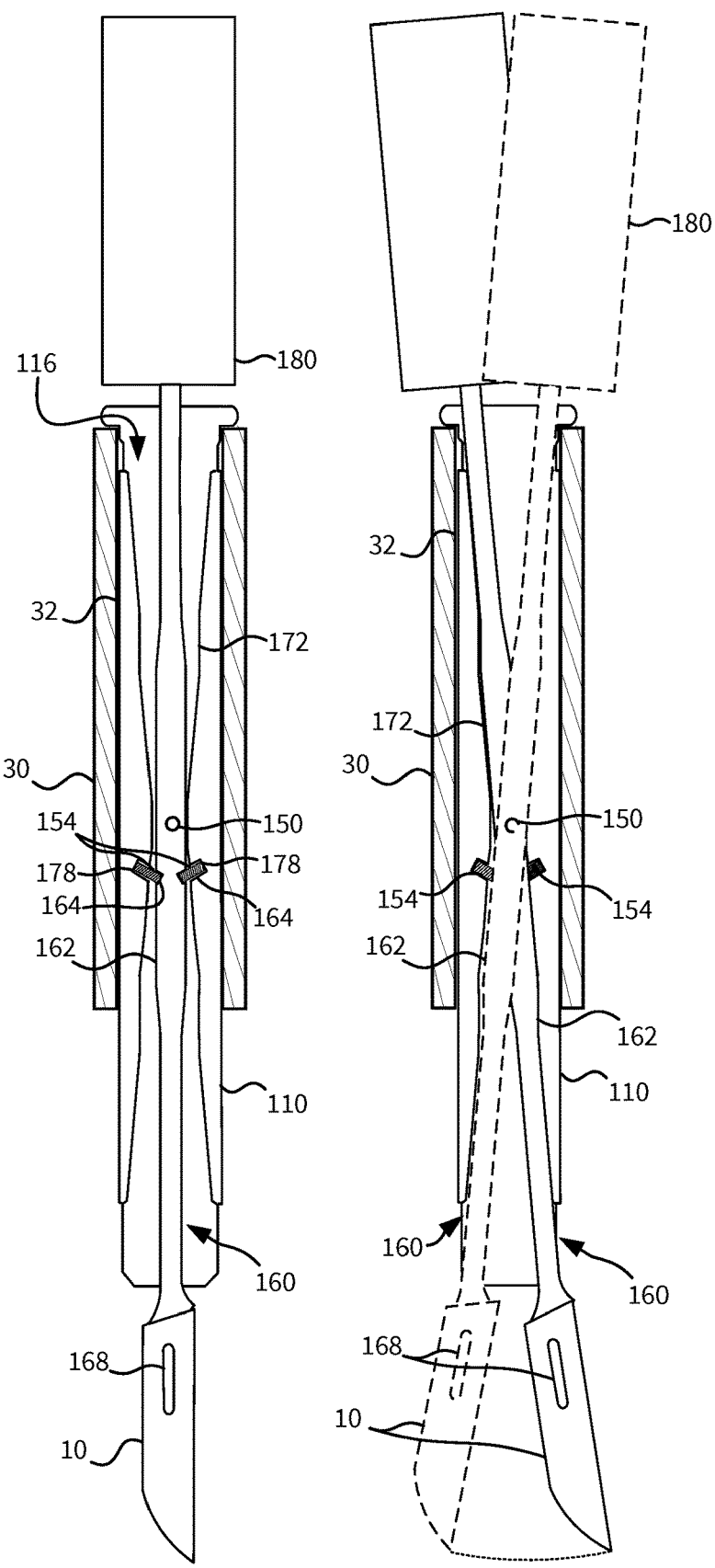
FIG. 6　　FIG. 7　　FIG. 8

CUTTING APPARATUS

BACKGROUND

A wide variety of surgical assemblies and systems have been developed. Some of these assemblies and systems include instruments used in spinal surgeries. These assemblies and systems are manufactured by any one of a variety of different manufacturing methods and may be used according to any one of a variety of methods. Of the known medical assemblies, systems, and methods, each has certain advantages and disadvantages.

Guide tubes can assist in performing surgical procedures on a patient. A robotic or analog mechanical arm can hold a guide tube at a desired location relative to the patient's anatomy. A surgeon uses the guide tube to guide surgical instruments along a desired trajectory to treat the patient.

SUMMARY

An example surgical cutting apparatus includes: a housing defining a scalpel guide; a scalpel longer than a length of the housing and having a movement path constrained by the scalpel guide; a handle coupled to a proximal end of the scalpel; and a blade holder at a distal end of the scalpel.

Continuing the example surgical cutting apparatus, the scalpel of can be pivotably coupled to the housing. The handle can further include a lock configured to resist the scalpel pivoting in relation to the housing. The lock can include a lock tab. The housing can include a catch. The lock can be slidably disposed within a handle channel of the handle such that the lock tab can selectively fit within the catch to resist the scalpel moving in relation to the housing. The apparatus can be configured such that the scalpel moves relative to the housing when forming an incision. The scalpel can pivot about only a single pivot point or multiple pivot points. The blade holder can be the sole blade holder of the surgical cutting apparatus. The scalpel can be unitary. The handle can be fixed to the scalpel and rotates about the pivot point. The housing can include a housing pivot point. The apparatus can further include a pivot pin extending through the housing pivot point and the scalpel pivot point. The apparatus can include a biaser configured to bias the scalpel into a starting position. The biaser can include at least two springs biasing the scalpel toward parallel with a length of the housing. The apparatus can further include a guide tube of a robot arm. The housing can be disposed within the guide tube. The housing can further include a housing lip disposed at a proximal end of the housing. The housing lip can abut a proximal end of the guide tube, thereby resisting further distal movement of the housing through the guide tube. The housing can include a plurality of grooves extending parallel to the length of the housing. The guide tube can include a detent configured to interact with a groove of the plurality of to resist rotation of the housing within the guide tube. The housing can include a front housing and a back housing coupled together.

A second example system includes an arm holding a guide tube having a tube inner diameter and a cutting apparatus. The cutting apparatus includes a housing extending through the guide tube, a scalpel extending through the housing and having a blade disposed at a distal end of the scalpel. The scalpel is pivotably coupled to the housing such that the length of the swing of the distal tip of the blade is greater than the tube inner diameter.

Continuing the second example system, the housing can define a scalpel guide, which defines a movement plane in which the scalpel can move. The scalpel guide further constrains an angle of movement of the scalpel. The housing comprises a pivot pin about which the scalpel pivots.

An example method includes: inserting a cutting apparatus into a guide tube of a surgical robot such that a blade at a distal end of the cutting apparatus extends distal to a distal end of the guide tube and a handle at a proximal end of the swing scalpel is proximal to a proximal end of the guide tube; after inserting the swing scalpel, unlocking the cutting apparatus; laterally moving the handle in a first direction to a first position such that a tip of the blade reaches a first point by moving in an opposite direction; and laterally moving the handle in a second direction to a second position such that a tip of the blade reaches a second point by moving in an opposite direction. Either or both of the first point and the second point is outside of an inner diameter of the guide tube.

The example method can further include rotating the cutting apparatus in the guide tube such that a ball of the guide tube moves from a first groove of the housing of the cutting apparatus to a second groove of the housing of the cutting apparatus. The method can further include forming an incision with the blade such that a skin-level length of the incision is longer than an inner diameter of the guide tube. Forming the incision can include the step of laterally moving the handle in the second direction. Moving the handle to a first position can include overcoming at least one bias force that urges the tip of the blade toward a starting position. Moving the handle to a first position can include pivoting a scalpel arm of the cutting apparatus within a housing of the cutting apparatus. Unlocking the cutting apparatus can include sliding a lock tab from a first position in which a lock tab is disposed within a catch in the housing to a second position in which the lock tab is outside of the catch.

BRIEF DESCRIPTION OF THE DRAWINGS

FIG. 6 illustrates a cutaway view of the cutting apparatus inserted into the guide tube with the scalpel removed.

FIG. 7 illustrates a cutaway view of the cutting apparatus inserted into the guide tube with the scalpel in a starting position.

FIG. 8 illustrates the swinging of the scalpel being blocked by the scalpel guide.

DETAILED DESCRIPTION

An articulating arm holds a guide tube in a desired location proximate a target surgical site of a patient's anatomy. But forming an incision relative to the target surgical site and guide tube can be difficult. For example, forming an incision prior to positioning the guide tube may require the surgeon to predict or determine where the arm will hold the guide tube, which can lead to errors or somewhat defeat the usefulness of the guide tube. A surgeon may form the incision while the guide tube is in position, but manipulating a traditional scalpel through or around the guide tube can be difficult. The guide tube can be positioned so a user can make a mark or initial incision on the patient's skin through the guide tube, moved out of the way so a full incision can be formed, and then moved back to continue with the procedure. But such frequent moving can be inefficient. Disclosed examples include a cutting apparatus relevant to improving incision formation through a guide tube.

An example of such a cutting apparatus includes a scalpel that pivots about a pivot point within a scalpel housing placed in the guide tube. The cutting apparatus permits dynamic blade movement that reaches beyond the inner circumferential bounds of the distal end of the guide tube to create an incision that is longer than the inner diameter of the guide tube. A handle is coupled to the scalpel and is proximally outside of the housing and guide tube. A cutting blade is coupled to the scalpel and extends distally outside of the housing and the guide tube. The scalpel is locked in a straight position for introduction of the cutting apparatus through a guide tube. After passage through the guide tube, the cutting apparatus is unlocked, which allows for side-to-side swinging of the scalpel in a cutting plane. The side-to-side swinging motion of the scalpel is constrained by a scalpel guide, such as may be defined by the housing. The scalpel is biased toward the center straight position such that the user must overcome the bias force to swing the blade to make an incision. The cutting apparatus can be configured for use through a guide tube of set inner diameter. For instance, the cutting apparatus can be configured to have a close fit with the guide tube such that the cutting apparatus is guided by the guide tube sufficiently well to form an incision suitable for the desired procedure. An example cutting apparatus is shown and described in relation to FIGS. 1-3.

Figure 1:
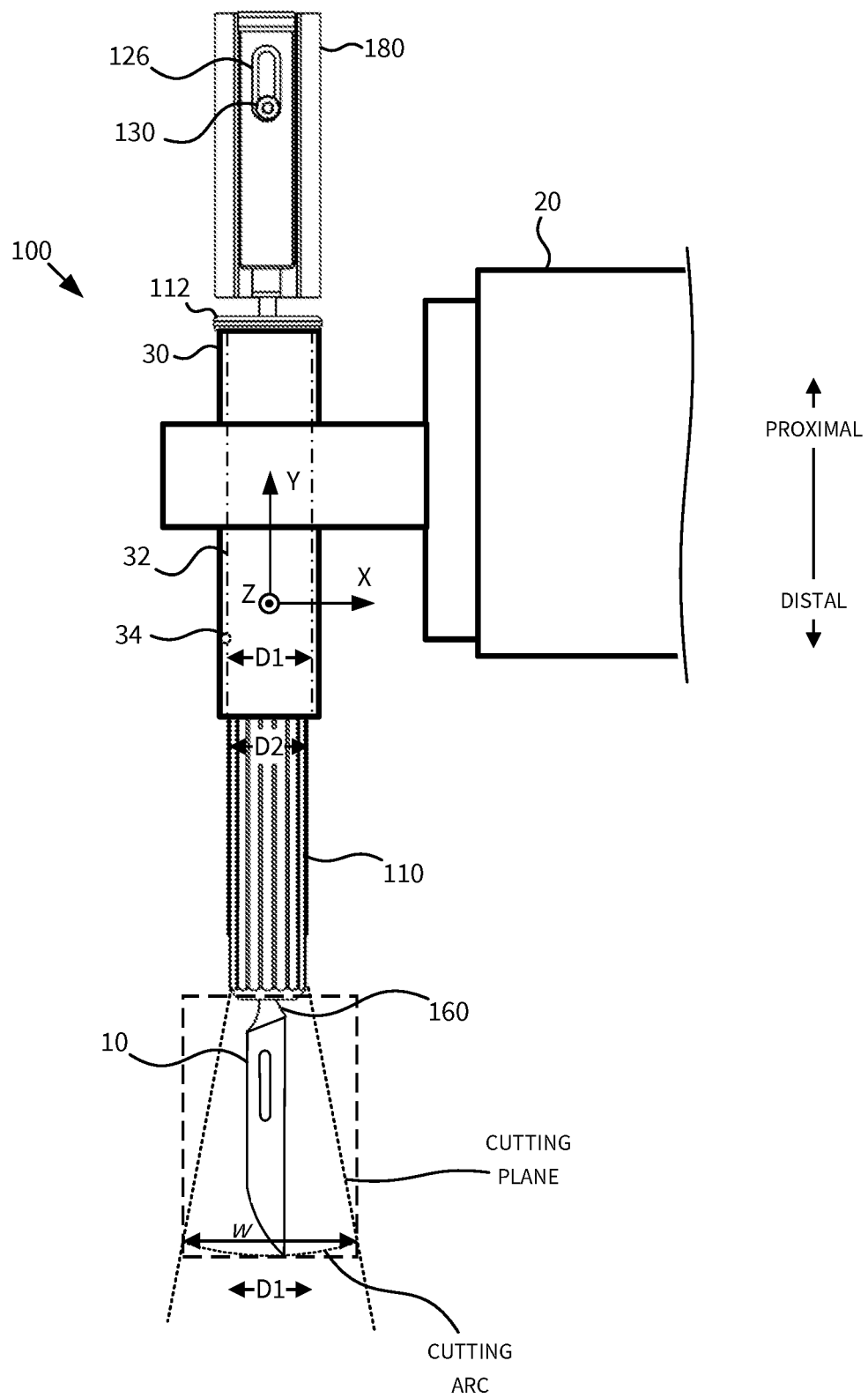
FIG. 1 illustrates a side view of an example cutting apparatus constrained by a guide tube held by an arm.
Figure 2:
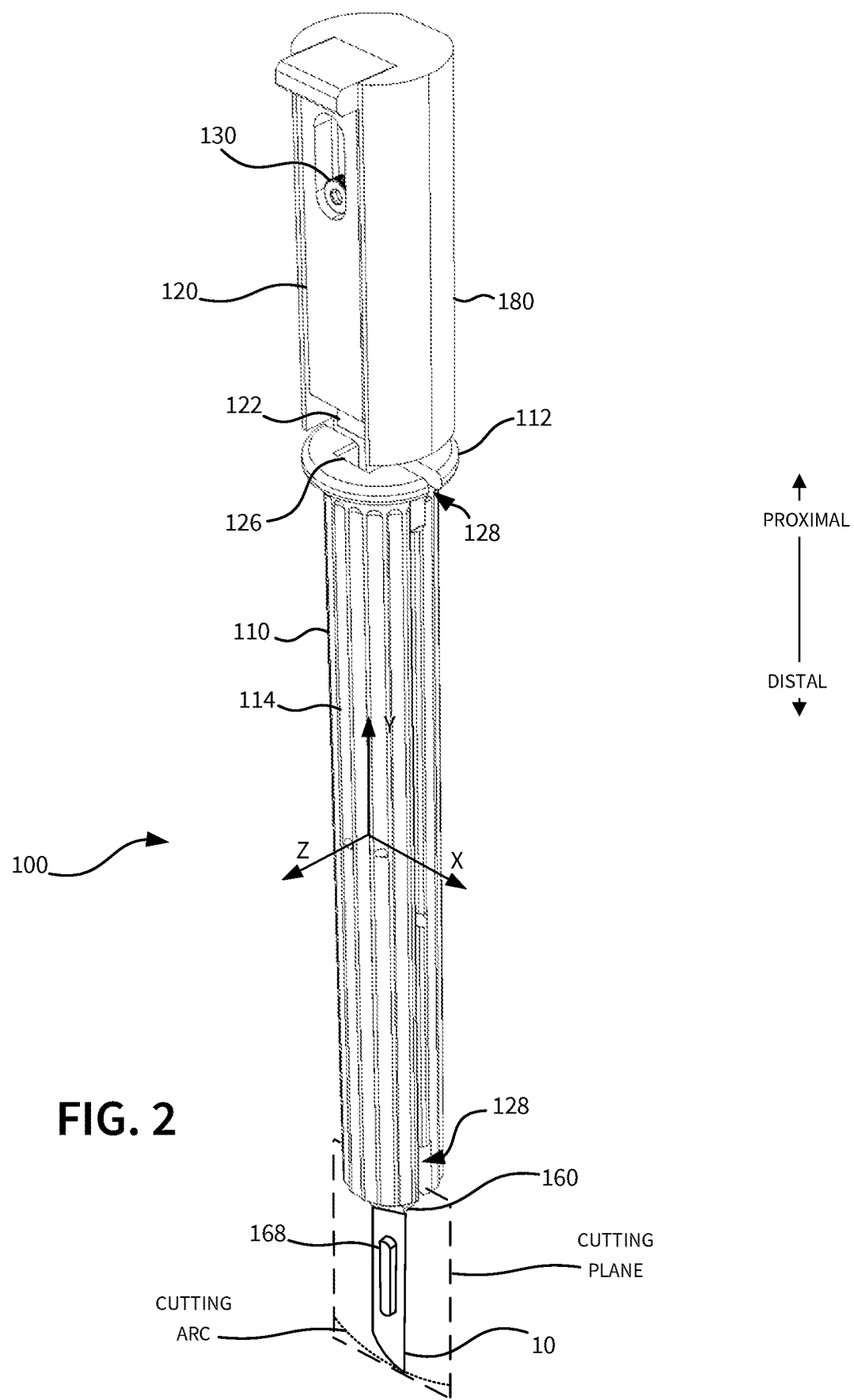
FIG. 2 illustrates a perspective view of the cutting apparatus.
Figure 3:
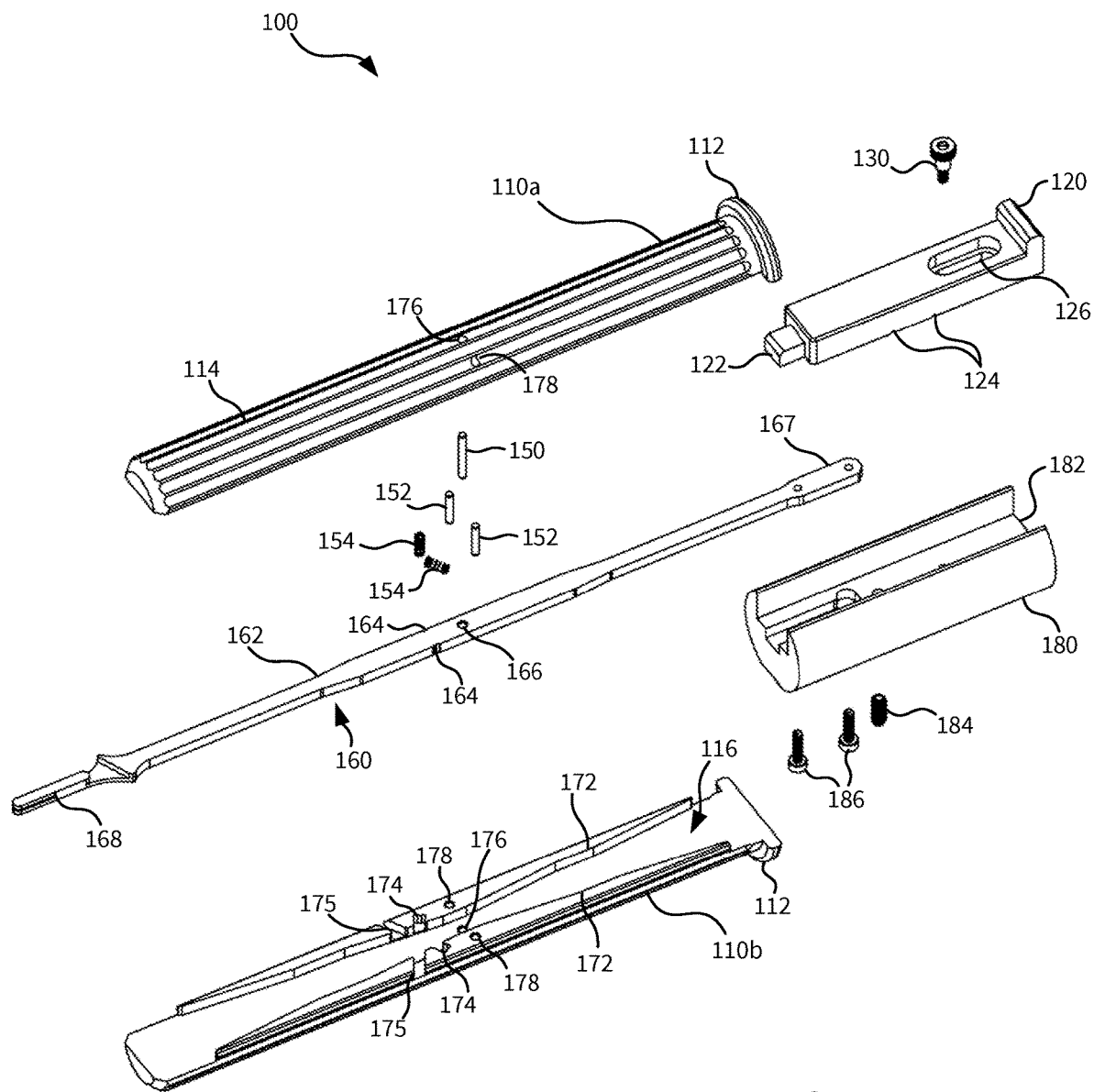
FIG. 3 illustrates an exploded view of the cutting apparatus.

FIG. 1 illustrates a side view of an example cutting apparatus 100 constrained by a guide tube 30 held by an arm 20. FIG. 2 illustrates a perspective view of the cutting apparatus 100. FIG. 3 illustrates an exploded view of the cutting apparatus 100.

The guide tube 30 can be an end effector or other component held by the arm 20, such as a robotic or non-robotic articulating arm. The guide tube 30 can be manually or automatically positioned in a desired location relative to a patient, typically close to but not in contact with the patient's tissue. The arm 20 can resist unwanted movement of the guide tube 30 out of that position. The guide tube 30 can define an inner passage 32 of diameter D1 through which instruments can be passed and guided. Instruments having a sufficient diameter can pass through and be guided by the guide tube 30, so as to follow a desired trajectory held by the arm 20. In some implementations, the guide tube 30 includes a ball 34 or other structure that can interact with one or more detents or grooves of an instrument (e.g., the cutting apparatus 100 or another instrument) to facilitate maintaining a particular rotation of the instrument within the guide tube 30.

In the illustrated example, the cutting apparatus 100 includes a housing 110 through which a scalpel 160 extends. A handle 180 and a blade 10 are coupled to the scalpel 160. As illustrated in FIG. 1, the cutting apparatus 100 can be described relative to X, Y, and Z axes having an origin at the center of the cutting apparatus 100. As illustrated, the Y axis corresponds to the length of the cutting apparatus 100 and defines a proximal direction (e.g., in a direction toward the end of the cutting apparatus 100 having the handle 180) and a distal direction (e.g., toward the end of the cutting apparatus 100 having the blade 10). The housing 110 is generally cylindrical and has a circumference defined in the X and Y directions. The cutting apparatus 100 defines a cutting plane in which the scalpel 160 moves the blade 10 and a cutting arc along which the tip of blade 10 moves. The cutting plane need not be perfectly planar and the cutting arc need not be perfectly arcuate. Manufacturing tolerances and user movement may contribute to irregularities in the path of the blade 10. The cutting plane may be sufficiently planar as to permit a user to form a sufficiently straight incision to perform a surgical procedure. The cutting apparatus 100 can be rotated in the guide tube 30 to angle the cutting plane in a desired direction.

The blade 10 can be a cutting blade, such as any of a variety of types of scalpel blades. Example blades 10 can be straight, curved, hooked, crescent-shaped, double sided, other kinds, or combinations thereof. The blade 10 can be configured to couple with a blade holder of the scalpel 160 according to a proprietary or industry standard coupling technique (e.g., ISO 7740:1985, entitled "Instruments for surgery—Scalpels with detachable blades—Fitting dimensions"). Further, while examples are primarily provided in the context of forming an incision, other kinds of surgical tools can be used in addition to or instead of the cutting apparatus 100. For example, disclosed embodiments can be adapted to be used with laser scalpels, ultrasonic knives, rasps, awls, taps, cutting burrs, rongeurs, scissors, saws, other tissue modification tools, or combinations thereof. Such tools can be guided by the guide tube 30 but still have a degree of movement to permit their use on tissue of the patient. Non-cutting tools can also be used, such as probes. For instance, the blade 10 could be replaced with a working portion of any of such cutting or non-cutting tools and the scalpel 160 and remainder of the cutting apparatus could be modified as needed to accommodate the change.

The housing 110 in the illustrated example generally provides an exterior that cooperates with the guide tube 30 and an interior that guides movement of the scalpel 160. In the illustrated example, the housing 110 is cylindrical in shape with a generally circular cross section. A distal end of the housing 110 can include a bevel to facilitate insertion of the housing 110 into the guide tube 30.

The housing 110 can be divided into a front housing 110a and a rear housing 110b. The divided sections of the housing 110 can be connected via fasteners 152. In the illustrated example, the fasteners 152 are pins disposed in housing connectors 178 to mate the housings 110a, 110b together. Example pins have a diameter of 1.5 mm, a length of 8 mm, are constructed from stainless steel, follow ISO 2338, and have an m6 tolerance class. The fasteners 152 can take other forms and alternative techniques may be used to assemble the housing 110, such as adhesives or welding.

The exterior of the housing 110 can be configured to interact with the guide tube 30. For example, the housing 110 can include a section have a maximum diameter D2 or width that is less than the internal diameter D1 of the guide tube 30 so that the portion of the housing 110 can fit within the guide tube. The difference between D1 and D2 can be selected to balance ease of insertion of the cutting apparatus 100 into and through the guide tube 30 with the internal diameter D1 sufficiently constraining movement of the cutting apparatus 100 along the trajectory of the guide tube 30 to be useful. In some examples, the inner passage 32 of the guide tube 30 can be circumferentially bounded such that instruments enter or exit the inner passage 32 only through proximal and distal openings of the guide tube (e.g., the guide tube 30 can lack lateral openings or slots through which instruments can fully or partially pass through the guide tube 30).

A housing lip 112 can be coupled to or integral with the housing 110. In the illustrated example, the housing lip 112 is disposed at a proximal end of the housing 110. The housing lip 112 can be a portion of the housing 110 configured to interact with a proximal portion of the guide tube 30 to resist or prevent further distal movement the cutting apparatus 100 into the guide tube 30. For example, the housing lip 112 can have an outer diameter or width greater than that of the inner diameter D2 of the guide tube 30. As a result, the distal end of the cutting apparatus 100 can be inserted through the guide tube 30 until the housing lip 112 abuts the proximal end of the guide tube 30, thereby preventing further distal movement of the apparatus 100 relative to the guide tube 30.

The exterior of the housing 110 can define elongate grooves 114. In the illustrated example, each groove 114 extends along a length of the housing 110, and the plurality of grooves 114 is disposed circumferentially around the housing 110. The grooves 114 can receive the one or more balls 34 or other structure of the guide tube 30 to facilitate maintaining a particular rotation of the cutting apparatus 100 about the Y axis, thereby facilitating maintenance of a particular angle of the cutting plane (e.g., relative to the arm 20). For example, the one or more balls 34 can fit into one or more of the grooves to form one or more ball-and-detent structures that facilitate (but not necessarily lock) holding the cutting apparatus 100 in a particular angle about the Y axis.

The housing 110 can define a catch 126. The catch 126 can be a portion of the housing 110 in which a lock tab can be received to resist unwanted movement of the scalpel 160. As described in more detail below, the catch 126 can receive a lock tab of a lock coupled with the handle of the cutting apparatus 100 to resist unwanted movement of the scalpel 160 relative to the housing 110.

The housing 110 can define one or more recesses or breaks 128 that accommodate lateral movement of the scalpel 160 outside of the housing. For example, as illustrated, the proximal and distal ends of the housing 110 include breaks 128 parallel to the cutting plane that allow for movement of the scalpel without being constrained by the housing 110 at that location. The housing 110 defines proximal and distal breaks 128 that permit the scalpel 160 to have a wider range of motion than would otherwise be permitted by the housing 110. The breaks 128 can take the form of lateral cutaways in the housing 110 and the scalpel guide 172 into which the scalpel 160 can move. As illustrated, the breaks 128 extend partially, but not entirely, along the length of the housing 110. In some examples, each break 128 extends approximately 10% along the total length of the housing 110. In other examples, the breaks 128 extend entirely along the entirety of the housing 110.

Internally, the illustrated housing 110 defines a passage 116 through which the scalpel 160 extends and can move. The housing 110 defines a scalpel guide 172 that constrains movement of the scalpel 160 (e.g., by defining a shape of the passage 116). The scalpel guide 172 is one or more structures integral with or coupled to the housing 110. In the illustrated example, the scalpel guide 172 includes lateral walls that the scalpel 160 abuts if the scalpel 160 is pivoted or otherwise moved sufficiently far in a particular direction. In this manner, the scalpel guide 172 constrains the movement path of the scalpel 160. In the illustrated example, the scalpel guide 172 is relatively contoured to compliment a shape and position of the scalpel 160 when the scalpel 160 is moved to a furthest desired extend. For example, the scalpel guide 172 can be shaped and disposed such that the scalpel 160 contacts multiple portions of the scalpel guide 172 when movement of the scalpel 160 is halted by the scalpel guide 172. In other examples, the scalpel guide 172 may not be so contoured. In some examples, the scalpel guide 172 includes one or more pins or other structures that interrupt a motion path of the scalpel 160. In some examples, the scalpel guide 172 is a track in which the scalpel 160 (or a portion connected thereto) rides. In some examples, the shape, size, or position of the scalpel guide 172 is modifiable by the user so that custom cutting paths can be defined. For instance, a pin can be moved from a first holder to a second holder to change the amount of travel the scalpel 160 has before it contacts the pin. In another example, a user adjusts one or more gears to change a position of the scalpel guide 172. In a still further example, the scalpel guide 172 is slidable in a track but selectively locked in position by a user adjustable set screw. In yet further examples, the cutting apparatus may not substantially define the scalpel guide 172. Instead, a range of motion of the scalpel 160 may be limited by the guide tube 30.

The housing 110 can define one or more biaser holders 174 that hold one or more biasers 154. The biasers 154 can be one or more components of the cutting apparatus 100 that bias the scalpel 160 into or out of a particular position, such as a starting position. In the illustrated example, the particular position is one in which the scalpel 160 is parallel to a length of the housing 110. In other examples, the biaser 154 can bias the scalpel 160 such that it is pivoted to a particular side of the cutting apparatus 100 (e.g., corresponding to a starting point of an incision). In the illustrated example, the biaser 154 is formed from two springs each having an end seated in a respective biaser holder 174 of the housing 110 and another end interacting (e.g., coupled with) a biaser connection portion 164 of the scalpel 160. As the scalpel 160 is pivoted in one direction, one of the biasers 154 is lengthened and the other biaser 154 is compressed. The compression and lengthening resists the pivoting and urges the scalpel 160 to return to a position in which the springs are relatively balanced. The biasers 154 can take other forms, such as magnets that interact with one or more magnets disposed at the scalpel 160. In some examples, in addition to or instead of walls of the scalpel guide 172, the biaser 154 can constrain the movement of the scalpel 160. For instance, the biaser 154 may compress or move for a distance, but then become sufficiently incompressible as to resist further movement of a scalpel 160 by a user. Such movement can be customized (e.g., during manufacturing or during use) to set the permitted range of movement.

The housing 110 can further include one or more biaser passages 175 through the housing 110 and scalpel guide 172 that permit the insertion of the biasers 154 during a manufacturing or assembly process. The passages 175 can be aligned with a long axis of the biaser holders 174 to aid in insertion of the baiasers 154.

The scalpel 160 is a portion of the cutting apparatus 100 that moves to cut tissue. The scalpel 160 includes an elongate scalpel arm 162 forming the body of the scalpel 160. The scalpel arm 162 can be a unitary structure having a length greater than a length of the housing 110. The scalpel 160 can include a biaser connection portion 164, a pivot point 166, a proximal connector 167, and a blade holder 168. The scalpel 160 can be configured to rotate relative to the housing 110 when forming an incision (e.g., rotate in a direction parallel to a length of the housing 110).

The biaser connection portion 164 is the portion of the scalpel 160 that interacts with a biaser 154 of the cutting apparatus 100. For example, the biaser connection portion 164 can be a cutout portion or a recessed portion configured to receive a portion of the biaser 154. The biaser connection portion 164 can define a shape or include a component configured to couple with the biaser 154. The biaser connection portion 164 can include a peg or other structure to encourage the biaser 154 stay in appropriate relation to the biaser connection portion 164 (e.g., resist drifting or movement of the biaser 154 away from the biaser connection portion 164). In some examples, (e.g., where the biaser 154 is a magnet, the biaser connection portion 164 may be a magnet, a portion holding a magnet, or a magnetic material.

The pivot point 166 is a point by which the scalpel 160 is pivotably coupled to the housing 110. The pivot point 166 can be a portion about which the scalpel 160 rotates relative to the housing 110. In an example, the pivot point 166 is a fixed point on the scalpel 160. For example, the housing 110 can include one or more housing pivot points 176 (e.g., each of the front housing 110a and the rear housing 110b can have a respective housing pivot point 176) aligned with the scalpel pivot point 166. The housing pivot point 176 can be fixed. A pivot pin 150 extends through the one or more housing pivot points 176. In an example, the pivot pin 150 has a diameter of 1.5 mm, a length of 12 mm, is constructed from stainless steel, follows ISO 2338, and has an m6 tolerance class. In an example, the pivot pin 150 is non-translating (e.g., the pivot pin 150 may rotate, but it does not travel through path, such as a cam channel). In an example, the pivot point 166 is the only pivot point about which the scalpel 160 moves when forming an incision. In an example, the pivot point 166 is the only pivot point about which a component of the apparatus 100 moves when forming an incision. The pivoting relationship between the scalpel 160 and the pivot point 166 can result in the scalpel 160 forming an incision having a variable depth (e.g., is arcuate when viewed perpendicular to the cutting plane). In an example, the pivoting connection (e.g., achieved via the pivot pin 150) between the scalpel 160 and the housing 110 can resist the scalpel 160 from moving proximally or distally (e.g., along the Y axis) relative to the housing 110 as well as resist the scalpel from substantially rotating outside of the cutting plane (e.g., resisting rotation of the scalpel 160 about the Y or X axes). In some examples, such restriction of movement may be achieved by the housing 110 itself (e.g., the passage 116 not being sized to substantially permit such movement). In other examples, the pivot pin 166 can be translating, such as following a cam channel defined in one or both of the scalpel 160 and the housing 110. The pivot point 166 may be one of multiple different pivot points of the cutting apparatus 100 that facilitates cutting action.

The blade holder 168 is a portion of the scalpel 160 configured to hold the blade 10. The blade holder 168 can be a region of the scalpel 160 that is unitary with the scalpel arm 162. The blade holder 168 can be disposed at a distal region of the scalpel 160. The blade holder 168 can configured in any of a variety of ways to securely hold the blade 10 for use. The blade holder 168 can secure the blade 10 in an industry standard manner, such as according to BS 2982:1992 ("Specification for Materials and Packaging of Surgical Scalpels with Detachable Blades") or ISO 7740: 1985 ("Instruments for surgery—Scalpels with detachable blades—Fitting dimensions"). An example description of a blade holder 168 and compatible blade 10 is provided at FIGS. 1-4 of U.S. Pat. No. 4,270,416, which is incorporated herein by reference in its entirety for any and all purposes. In an example, the blade holder 168 is the only blade holder of the apparatus 100. In other examples, the cutting apparatus can include multiple blade holders 168. In some examples, a single blade holder 168 may be beneficial over multiple blade holders 168 as an incision formed with a single blade may be cleaner (e.g., less ragged) than an incision formed with multiple blades. Further, a single blade may be easier fora user to control than multiple blades. In some examples, the blade holder 168 and the blade 10 are integral or are not configured to be user separable.

The proximal connector 167 can be a portion of the scalpel 160 configured to couple with the handle 180. For example, in the illustrated example, the proximal connector 167 includes two holes into which fasteners 186 can connect to couple the handle 180. In an example, the fasteners 186 are stainless steel socket head screws having a length of 8 mm and a diameter of 2 mm.

The scalpel 160 can lack a portion by which the user directly grasps when forming an incision. The user instead directly grasps the handle 180, which is coupled with the proximal end of the scalpel 160. As a result, movement of the handle 180 directly causes movement of the scalpel 160. Further, the movement of the handle 180 is indirectly constrained by the scalpel guide 172 because the scalpel guide 172 constrains movement of the scalpel 160 and the handle 180 is directly coupled to the scalpel 160. The connection between the scalpel 160 and the handle 180 results in the handle 180 rotating about the pivot point 166. The rotation of the handle 180 about the pivot point 166 in the cutting plane causes rotational movement of the scalpel 160 in the cutting plane.

The handle 180 is a portion configured to be held by a user's hand for controlling the scalpel 160. In an example, the handle 180 is the only portion by which the use grasps the cutting apparatus during use to form an incision. The handle 180 can be configured for grasping based on its size, position, or surface features (e.g., grips or knurling) 100. In an example, the handle 180 is sized to accommodate grasping by the user. The handle 180 can have a width (or diameter where the handle 180 has a circular cross-section) that is greater than a width of the scalpel 160, than the inner diameter of the guide tube 30, than the width of the distal end of the housing 110, and/or greater than a width of the lip 112. In an example, the handle 180 is elongate (e.g., longer in the Y direction than it is in the X or Z directions).

Figure 4:
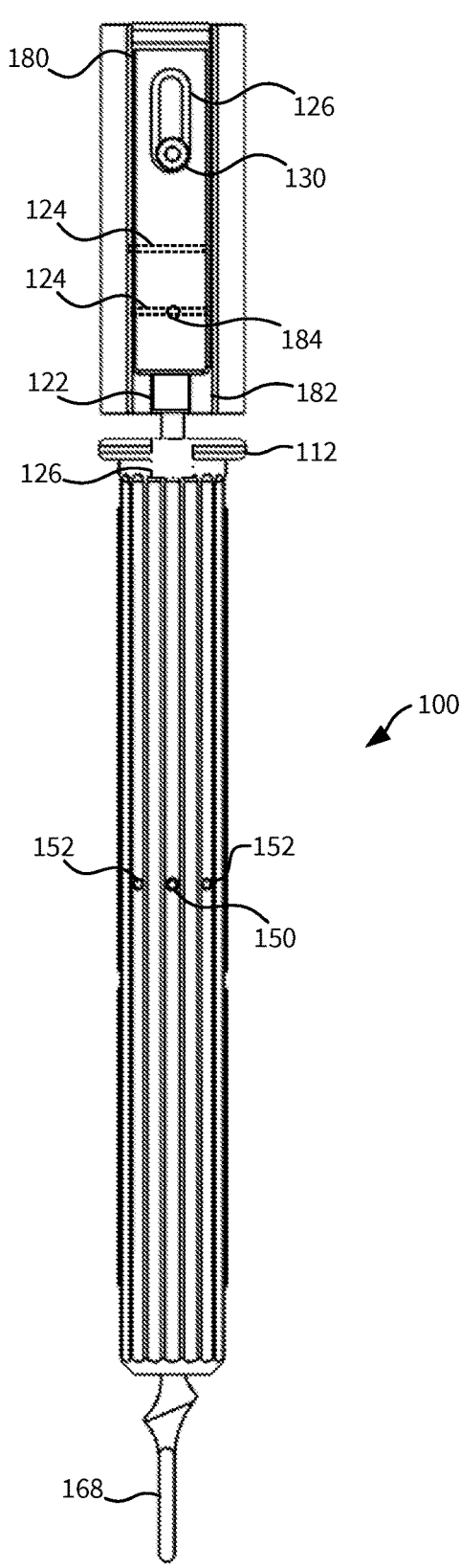
FIG. 4 illustrates a side view of the cutting apparatus in an unlocked configuration.
Figure 5:
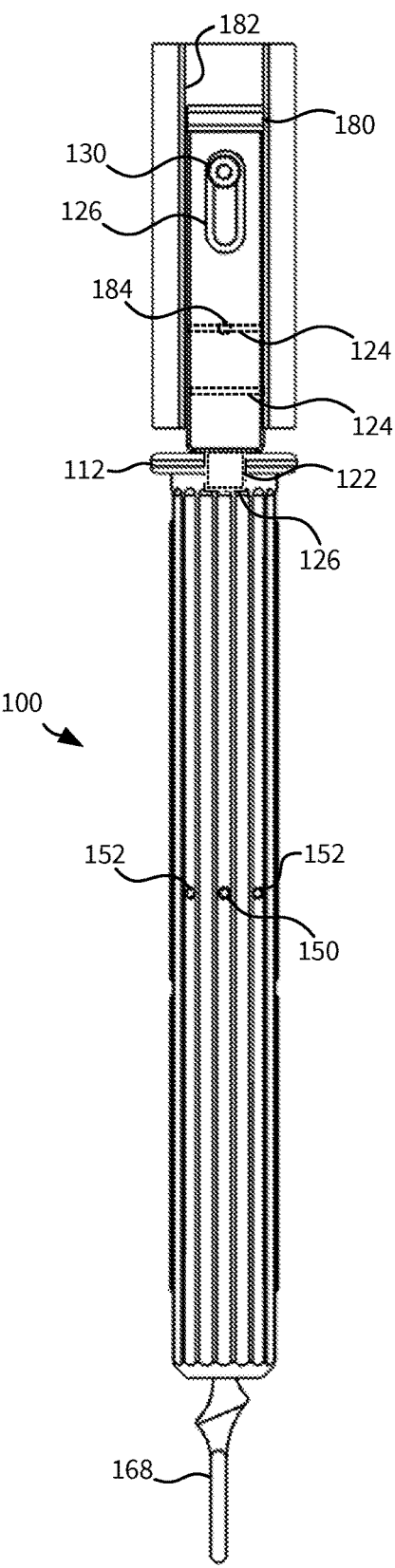
FIG. 5 illustrates a side view of the cutting apparatus in a locked configuration.

In the illustrated configuration, the handle 180 defines a longitudinal handle channel 182 and includes a lock ball 184. Disposed within the handle channel 182 is a lock 120. The lock 120 is a component configured to resist the scalpel 160 pivoting in relation to the housing 110. The lock 120 is in a sliding relationship with the handle 180. The lock 120 is coupled to the handle via a shoulder screw 130 that slides within a lock channel 126. The lock 120 includes a lock tab 122. In an example, the lock 120 is slidably disposed within a handle channel 182 of the handle such that the lock tab 122 can selectively fit within the catch 126 to resist the handle 180 moving in relation to the housing 110 (e.g., thereby resisting the scalpel 160 from moving in relation to the housing 110). The lock 120 can include at least two lock detents 124 that cooperate with the lock ball 184. As shown in FIG. 4, when the lock ball 184 is engaged with a first lock detent 124, the engagement retains the lock 120 in an unlocked position, but the engagement can be overcome with sufficient force. To enter the locked position, the lock 120 is slid distally in the handle 180 until the lock tab 122 is disposed within the catch 126 of the housing 110. The lock tab 122 being disposed within the catch 126 resists movement of the handle 180, which also resists movement of the scalpel 160 due to the connection between the handle 180 and the scalpel 160. To enter an unlocked position, the lock 120 is slid proximally until the lock tab 122 leaves the catch 126 of the housing 110. Sufficient proximal movement can result in the second lock detent 124 being engaged with the lock ball 184, which can resist the lock 120 falling back into the locked position. As shown in FIG. 5, when the lock ball 184 is engaged with a second lock detent 124, the engagement retains the lock 120 in a locked position, but the engagement can be overcome with sufficient force. With the lock tab 122 no longer constrained by the catch 126, the handle 180 (and coupled scalpel 160) is free to translate laterally (e.g., as a part of the handle 180 rotating about the pivot point 166) to cause movement of the blade 10.

FIG. 6 illustrates a cutaway view of the cutting apparatus 100 inserted into the guide tube 30 with the scalpel 160 removed so the scalpel guide 172 can more clearly be viewed. The housing lip 112 rests on the proximal end of the guide tube 30.

FIG. 7 illustrates a cutaway view of the cutting apparatus 100 inserted into the guide tube 30 with the scalpel 160 in a starting position. In this illustrated example, the starting position of the scalpel 160 is one in which the length of the scalpel 160 is perpendicular to the length of the housing 110. In an example implementation, the forces of the biasers 154 on the scalpel 160 is balanced while in the starting position.

FIG. 8 illustrates the swinging of the scalpel 160 being blocked by the scalpel guide 172. In an example, the angle of rotation of the scalpel 160 permitted by the scalpel guide 172 is ten degrees. In other examples, the angle of rotation can be more or less.

Figure 9:
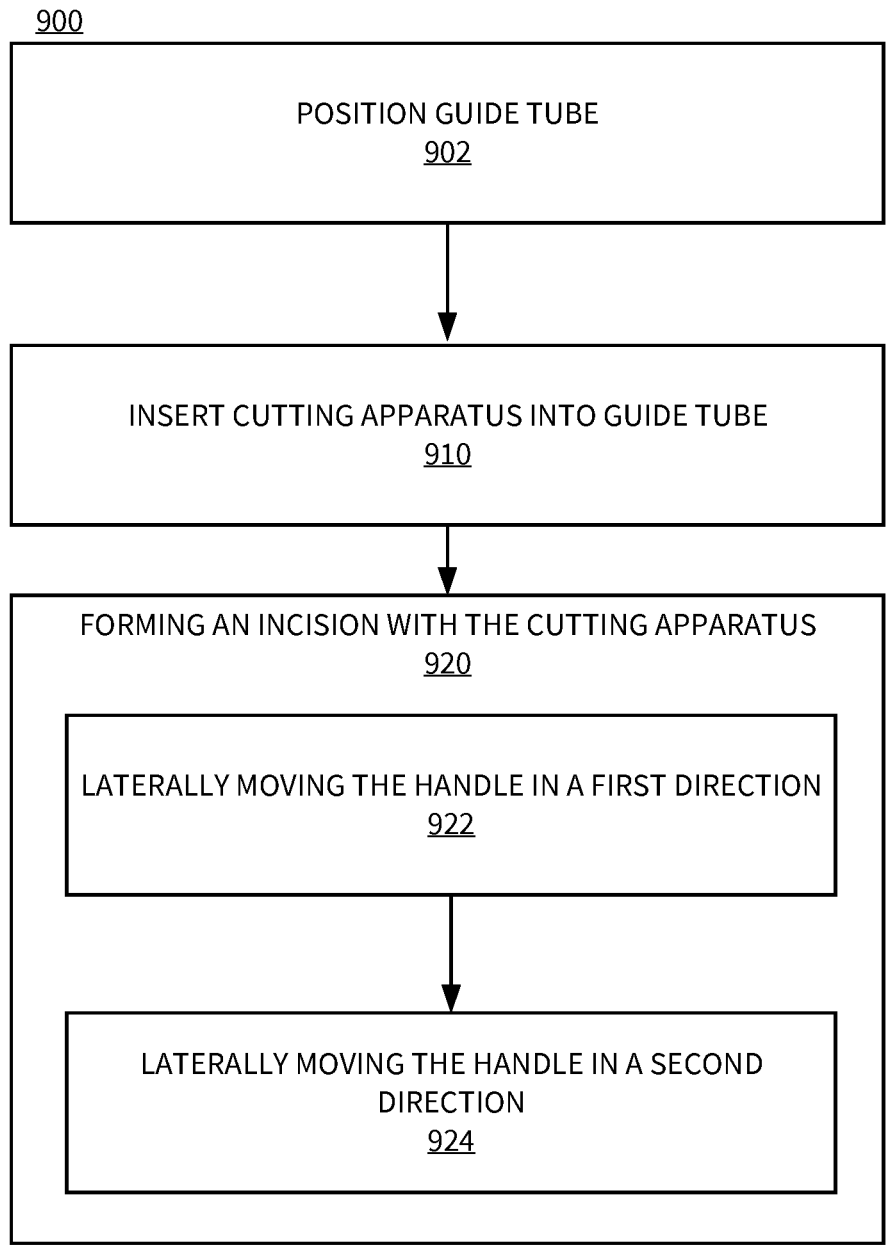
FIG. 9 illustrates an example method for using the cutting apparatus.

FIG. 9 illustrates an example method 900 for using the cutting apparatus 100. The method 900 can begin with operation 902. Operation 902 includes positioning a guide tube 30. The guide tube 30 can be positioned relative to a surgical target site, such as by a patient's spine when the guide tube 30 is being used for a spinal procedure. In some examples the guide tube 30 is positioned a specific distance away from the patient's skin to accommodate the cutting apparatus 100 and to allow formation of an incision having a desired depth. The guide tube 30 can be coupled to a robot arm and positioning the guide tube 30 can include the robot arm being manually guided by a user (e.g., the robot arm receives user input that guides the robot arm to a desired position) so that the guide tube 30 is in a desired position. In other examples, the robot arm is programmed to automatically move the guide tube 30 to the desired position. In some examples, the guide tube 30 is held by a non-robotic lockable articulated holding arm 20. The guide tube 30 can be positioned and then the arm locked in place. Following operation 902, the flow of the method can move to operation 910.

Operation 910 includes inserting the cutting apparatus 100 into a guide tube 30. This operation can include inserting the cutting apparatus 100 into the guide tube 30 until the housing lip 112 is in contact with a proximal end of the guide tube 30 such that further advancement of the cutting apparatus 100 is blocked (see, e.g., FIG. 6), though the cutting apparatus 100 need not be inserted that far. In some examples, the cutting apparatus 100 is inserted into the guide tube 30 in a locked configuration. After or during advancement, the cutting apparatus 100 is unlocked such that the scalpel 160 can rotate about the pivot point 166. Unlocking the cutting apparatus 100 can include sliding the lock tab 122 from a first position in which a lock tab 122 is disposed within the catch 126 (see, e.g., FIG. 5) in the housing 110 to a second position in which the lock tab 122 is outside of the catch 126 (see, e.g., FIG. 4). In some instances, the cutting apparatus 100 is partially inserted while in the locked configuration, then the apparatus 100 is unlocked and the advancement continues In some examples, operation 910 includes or is related to an operation in which the cutting apparatus 100 is rotated relative to the guide tube. For instance, the cutting apparatus can be rotated in the guide tube 30 such that a ball 34 of the guide tube 30 moves from a first groove 114 of the housing 110 to a second groove 114 of the housing 110. Following operation 910, the flow of the method 900 can move to operation 920.

Operation 920 includes forming an incision with the cutting apparatus 100. The incision can be formed in any of a variety of ways. Generally, a user can form an incision via inserting the blade 10 into the patient's tissue and moving the handle 180. For example, the operation 920 can include operation 922, which includes laterally moving the handle 180 in a first direction to a first position such that a tip of the blade 10 reaches a first point by moving in an opposite direction. Following operation 922, the flow of the method 900 can move to operation 924, which includes laterally moving the handle in a second direction to a second position such that a tip of the blade 10 reaches a second point by moving in an opposite direction. The lateral movement of operations 922, 924 can be caused by rotating the handle 180 about the pivot point 166.

This movement may be resisted by bias forces provided by the one or more biasers 154. The moving may include overcoming at least one bias force that urges the tip of the blade 10 toward a starting position. In an example, either or both of the first point and the second point is outside of an inner diameter of the guide tube. The moving can include pivoting the scalpel arm 162 of the cutting apparatus 100 within the housing 110 by moving the handle 180. In some examples, the resulting incision has a skin-level length longer than an inner diameter of the guide tube 30. In some examples, the movement is halted by the scalpel guide 172 or the user stops the movement before the scalpel guide 172 does. A first example is shown in FIGS. 10-13 and a second example is shown in FIGS. 14-17.

Figure 10:
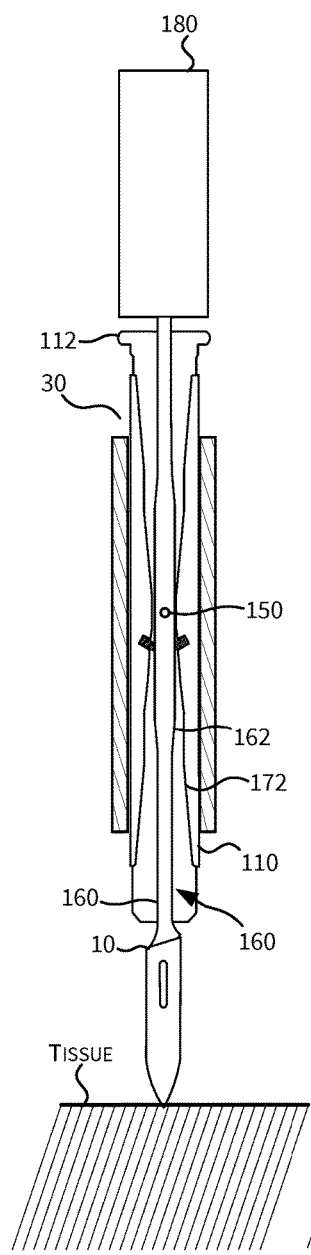
FIG. 10 illustrates a partial cutaway view of the cutting apparatus being inserted through the guide tube while the cutting apparatus is in a locked position and the scalpel is in an initial position substantially parallel with the length of the guide tube.
Figure 11:
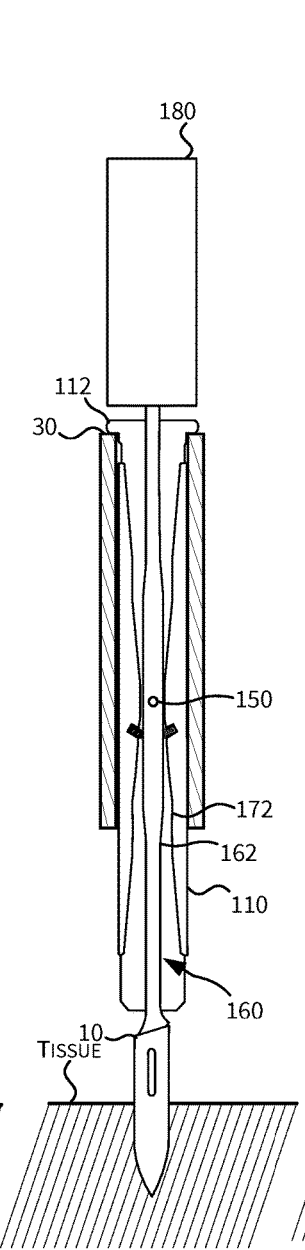
FIG. 11 illustrates a partial cutaway view of the cutting apparatus of FIG. 10 continuing to be inserted and the blade piercing the patient's tissue.
Figure 12:
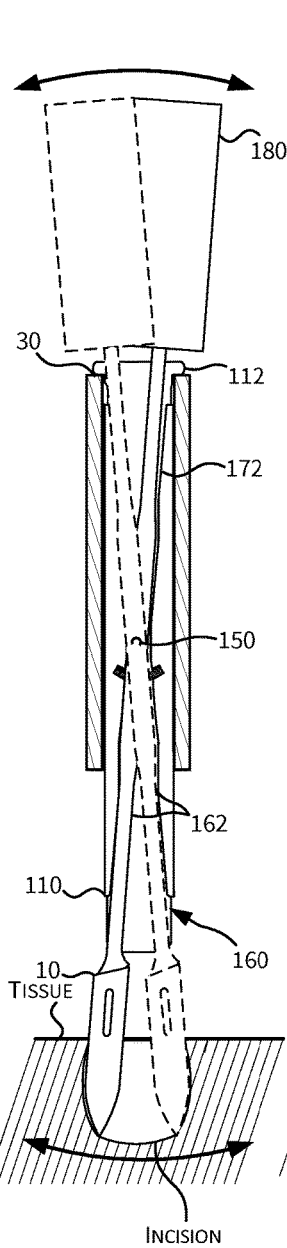
FIG. 12 illustrates a partial cutaway view of the cutting apparatus of FIG. 11 as its handle is swung from side to side to form an incision.
Figure 13:
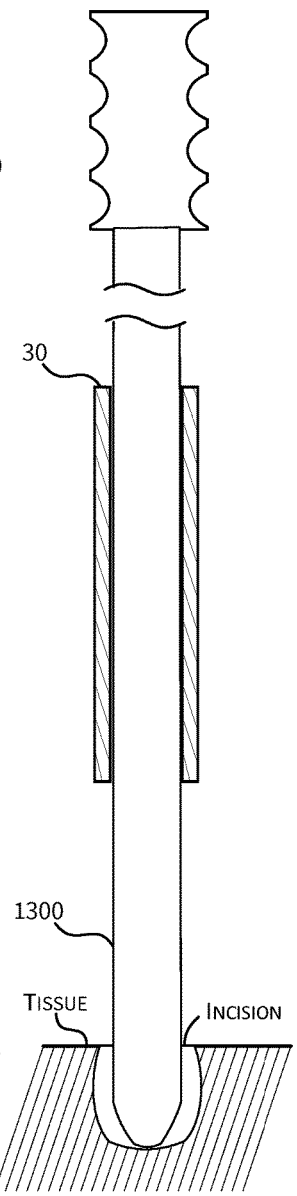
FIG. 13 illustrates a partial cutaway view after the cutting apparatus of FIG. 12 has been removed and a subsequent instrument provided in its place.

FIG. 10 illustrates the cutting apparatus 100 being inserted through the guide tube 30 while the cutting apparatus 100 is in a locked position and the scalpel 160 is in an initial position substantially parallel with the length of the guide tube 30. As illustrated, an outer diameter of the housing 110 is sufficiently close to the inner diameter of the guide tube 30 that the guide tube 30 guides the trajectory of the cutting apparatus 100 with sufficiently small margin of error for its use in the surgical procedure. Coupled to the scalpel 160 is a double sided blade 10 (e.g., a #40 scalpel blade) to facilitate cutting in two directions. The cutting apparatus 100 continues to be inserted and the blade 10 pierces the patient's tissue as shown in FIG. 11. The cutting apparatus 100 is then unlocked and, as shown in FIG. 12, the user swings the handle 180 side to side, which causes the blade 10 to move side to side and form an incision. Following formation of the incision, the cutting apparatus 100 is removed. A subsequent instrument 1300 for the procedure (e.g., a dilator as shown in FIG. 13) is then inserted through and guided by the guide tube 30. The guide tube 30 may be in the same position or a different position between being used to guide the cutting apparatus 100 and being used to guide the subsequent instrument 1300.

Figures 14, 15, 16, 17:
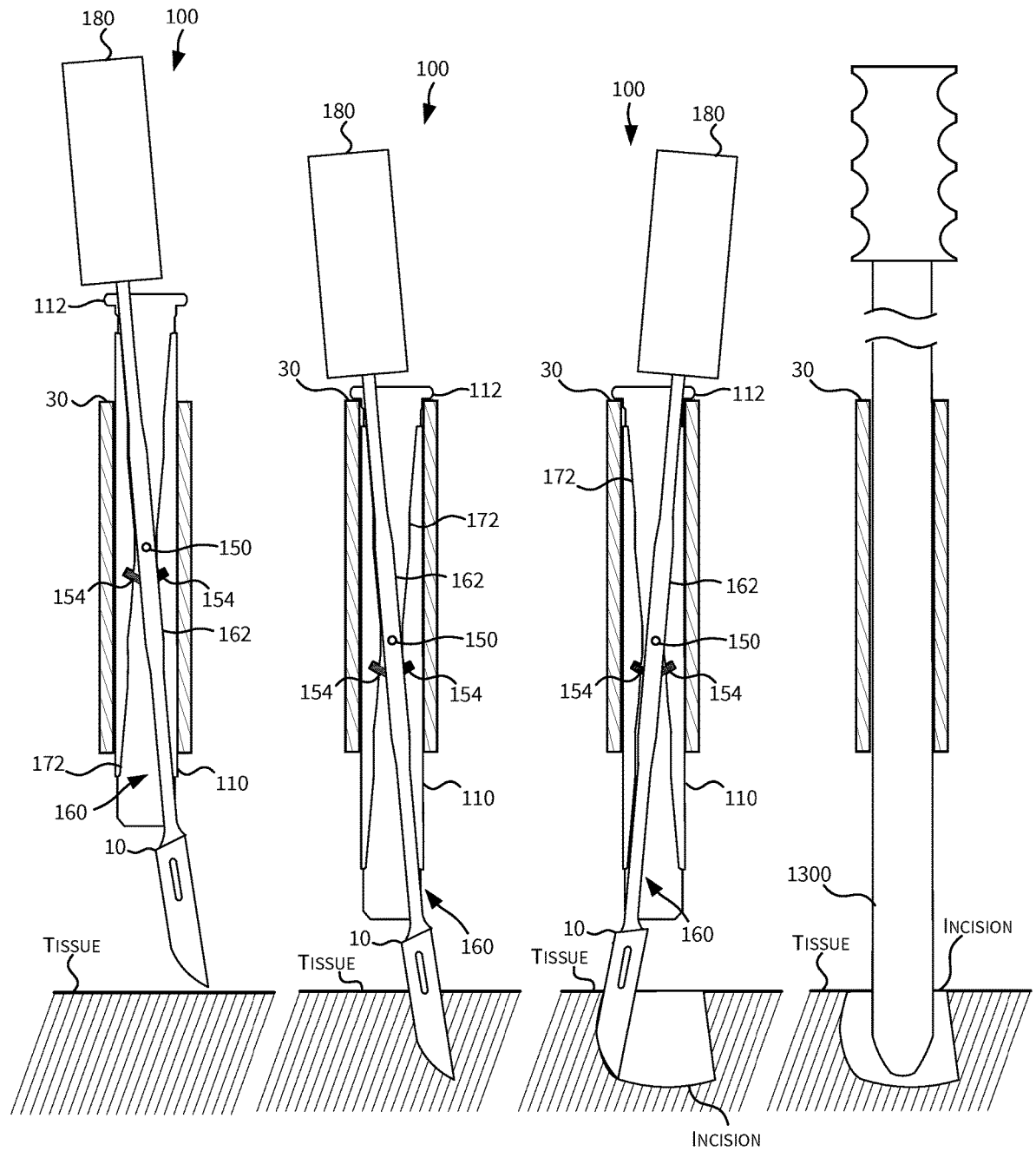
FIG. 14 illustrates a partial cutaway view of the cutting apparatus being inserted through the guide tube while the scalpel is swung to one side.
FIG. 15 illustrates a partial cutaway view of the cutting apparatus of FIG. 14 continuing to be inserted and the blade piercing the patient's tissue.
FIG. 16 illustrates a partial cutaway view of the cutting apparatus of FIG. 15 after its handle was swung to an opposite side to form an incision.
FIG. 17 illustrates a partial cutaway view after the cutting apparatus of FIG. 16 has been removed and a subsequent instrument provided in its place.

FIG. 14 illustrates the cutting apparatus 100 being inserted through the guide tube 30 while the cutting apparatus 100 is in an unlocked position and the scalpel 160 is swung to one side. The cutting apparatus 100 may have been initially inserted into the guide tube 30 while in a locked position and the scalpel 160 being in an initial position and then subsequently unlocked and moved to arrive at the configuration shown in FIG. 14. In other implementations, the scalpel being swung to one side is the starting position of the scalpel 160 (e.g., the one or more biasers 154 are configured to resist movement of the scalpel 160 out of this position) and the scalpel 160 may be locked in this position and need be unlocked to leave this position. Coupled to the scalpel 160 is a single sided blade 10. While swung to one side, the cutting apparatus 100 continues to be advanced through the guide tube 30 and the blade 10 enters the tissue to begin to form the incision as shown in FIG. 15. The user then swings the handle toward the opposite side, which causes the blade 10 to form a longer incision and reach the position shown in FIG. 16. Following formation of the incision, the cutting apparatus 100 is removed. A subsequent instrument 1300 for the procedure (e.g., a dilator as shown in FIG. 17) is then inserted through and guided by the guide tube 30.

In another example, prior to the blade 10 piercing the patient's skin, the handle 180 can be moved such that the scalpel 160 pivots to place the blade 10 in a desired starting position. The cutting apparatus 100 is then advanced such that the blade enters the patient's skin and then the handle is swung in the other direction to form the incision.

Although certain embodiments and examples are provided in the foregoing description, the inventive subject matter extends beyond the specifically disclosed embodiments to other alternative embodiments and/or uses, and to modifications and equivalents thereof. Thus, the scope of the claims appended hereto is not limited by any of the particular embodiments described herein. For example, in any method disclosed herein, the operations may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the systems, and/or devices described herein may be embodied as integrated components or as separate components.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

What is claimed is:

1. A surgical cutting apparatus comprising:
a housing defining a scalpel guide;
a scalpel longer than a length of the housing and having a movement path constrained by the scalpel guide;
a handle coupled to a proximal end of the scalpel; and
a blade holder at a distal end of the scalpel,
wherein the scalpel is pivotably coupled to the housing, and
wherein the handle further comprises a lock configured to selectively resist the scalpel pivoting in relation to the housing.

2. The apparatus of claim 1,
wherein the lock comprises a lock tab;
wherein the housing includes a catch; and
wherein the lock is slidably disposed within a handle channel of the handle such that the lock tab can selectively fit within the catch to resist the scalpel moving in relation to the housing.

3. The apparatus of claim 1,
wherein the apparatus is configured such that the scalpel moves relative to the housing when forming an incision;
wherein the scalpel pivots about only a single pivot point;
wherein the blade holder is the sole blade holder of the surgical cutting apparatus;
wherein the scalpel is unitary; and
wherein the handle is fixed to the scalpel and rotates about the pivot point.

4. The apparatus of claim 1,
wherein the scalpel comprises a scalpel pivot point;
wherein the housing comprises a housing pivot point; and
wherein the apparatus further comprises a pivot pin connecting the housing pivot point and the scalpel pivot point.

5. The apparatus of claim 1, further comprising:
a biaser configured to bias the scalpel toward a starting position.

6. The apparatus of claim 5,
wherein the biaser includes at least two springs; and
wherein, while in the starting position, the scalpel is parallel with a length of the housing.

7. The apparatus of claim 1, further comprising:
a guide tube of a robot arm,
wherein the housing is disposed within the guide tube.

8. The apparatus of claim 7,
wherein the housing further comprises a housing lip disposed at a proximal end of the housing,
wherein the housing lip abuts a proximal end of the guide tube, thereby resisting further distal movement of the housing through the guide tube.

9. The apparatus of claim 8,
wherein the housing comprises a plurality of grooves extending parallel to the length of the housing; and wherein the guide tube includes a detent configured to interact with a groove of the plurality of to resist rotation of the housing within the guide tube.

10. The apparatus of claim 1, wherein the housing comprises a front housing and a back housing coupled together.

11. A system comprising:
an arm holding a guide tube having a tube inner diameter; and
a cutting apparatus comprising:
a housing extending through the guide tube; and
a scalpel extending through the housing and having a blade disposed at a distal end of the scalpel,
wherein the scalpel is pivotably coupled to the housing such that a length of the full swing of the distal tip of the blade is greater than the tube inner diameter, and
wherein the housing comprises a pivot pin about which the scalpel pivots.

12. The apparatus of claim 11, wherein the housing defines a scalpel guide, which defines a movement plane in which the scalpel can move; and
wherein the scalpel guide further constrains an angle of movement of the scalpel.

13. A method comprising:
inserting a cutting apparatus into a guide tube of a surgical robot such that a blade at a distal end of the cutting apparatus extends distal to a distal end of the guide tube and a handle at a proximal end of the swing scalpel is proximal to a proximal end of the guide tube;
after inserting the cutting apparatus, unlocking the cutting apparatus;
laterally moving the handle in a first direction to a first position such that a tip of the blade reaches a first point by moving in an opposite direction; and
laterally moving the handle in a second direction to a second position such that a tip of the blade reaches a second point by moving in an opposite direction,
wherein either or both of the first point and the second point is outside of an inner diameter of the guide tube, and
wherein moving the handle to the first position includes overcoming at least one bias force that urges the tip of the blade toward a starting position.

14. The method of claim 13, further comprising:
rotating the cutting apparatus in the guide tube such that a ball of the guide tube moves from a first groove of the housing of the cutting apparatus to a second groove of the housing of the cutting apparatus.

15. The method of claim 13, further comprising:
forming an incision with the blade such that a skin-level length of the incision is longer than an inner diameter of the guide tube,
wherein forming the incision includes the step of laterally moving the handle in the second direction.

16. The method of claim 13, wherein moving the handle to a first position includes pivoting a scalpel arm of the cutting apparatus within a housing of the cutting apparatus; and
wherein unlocking the cutting apparatus includes sliding a lock tab from a first position in which a lock tab is disposed within a catch in the housing to a second position in which the lock tab is outside of the catch.

* * * * *